(12) United States Patent
Tahira et al.

(10) Patent No.: US 9,354,142 B2
(45) Date of Patent: May 31, 2016

(54) GAS SENSOR

(71) Applicant: NGK SPARK PLUG CO., LTD., Nagoya-shi, Aichi (JP)

(72) Inventors: Daisuke Tahira, Komaki (JP); Shingo Ito, Ichinomiya (JP); Keiichi Noda, Ichinomiya (JP); Yuichi Yamada, Komaki (JP); Makoto Kume, Inuyama (JP)

(73) Assignee: NGK SPARK PLUG CO., LTD., Aichi (JP)

( * ) Notice: Subject to any disclaimer, the term of this patent is extended or adjusted under 35 U.S.C. 154(b) by 194 days.

(21) Appl. No.: 14/278,241

(22) Filed: May 15, 2014

(65) Prior Publication Data

US 2014/0339081 A1   Nov. 20, 2014

(30) Foreign Application Priority Data

May 20, 2013  (JP) .................................. 2013-106474
Nov. 20, 2013  (JP) .................................. 2013-239722

(51) Int. Cl.
  *G01N 1/00*   (2006.01)
  *G01M 15/10*  (2006.01)
  *G01N 27/407* (2006.01)

(52) U.S. Cl.
  CPC .............. *G01N 1/00* (2013.01); *G01M 15/102* (2013.01); *G01N 27/407* (2013.01)

(58) Field of Classification Search
  CPC . G01M 15/10; G01M 15/102; G01M 15/104; G01N 1/2252; G01N 27/404–27/407; G01N 27/409; G01N 27/419; G01N 27/41; F01N 2560/00–2560/20; F01N 2550/00–2550/24; F01N 3/10; F01N 11/00
  See application file for complete search history.

(56) References Cited

U.S. PATENT DOCUMENTS

| | | | |
|---|---|---|---|
| 5,707,504 A | 1/1998 | Jyouno et al. | |
| 5,922,938 A | 7/1999 | Hafele | |
| 2008/0022754 A1 | 1/2008 | Nakagawa | |

(Continued)

FOREIGN PATENT DOCUMENTS

| | | |
|---|---|---|
| JP | 5-69669 U | 9/1993 |
| JP | 8-254521 A | 10/1996 |

(Continued)

OTHER PUBLICATIONS

Machine Translation JP2007017407A, Feb. 2, 2016.*

(Continued)

*Primary Examiner* — Jennifer Dieterle
(74) *Attorney, Agent, or Firm* — Sughrue Mion, PLLC

(57) ABSTRACT

Disclosed is a gas sensor including a metal shell, a ceramic holder placed in an axial inner hole of the metal shell and a sensor element inserted through an insertion hole of the ceramic holder. The ceramic holder has a recessed hole recessed toward the rear from a front-facing surface of the ceramic holder. The sensor element has, at a front end part thereof, a detection portion covered with a porous protection layer such that a rear end part of the protection layer is accommodated in the recessed hole with a space left therebetween. Further, the ceramic holder has a front circumferential edge defined between an inner circumferential surface of the recessed hole and the front-facing surface of the ceramic holder such that the whole of the front circumferential edge is located radially inside of a radially innermost position of the axial hole.

4 Claims, 9 Drawing Sheets

(56) References Cited

U.S. PATENT DOCUMENTS

| | | |
|---|---|---|
| 2008/0209984 A1 | 9/2008 | Yamada |
| 2009/0314056 A1 | 12/2009 | McCauley et al. |
| 2011/0283774 A1 | 11/2011 | Sekiya et al. |
| 2012/0211362 A1 | 8/2012 | Onkawa et al. |

FOREIGN PATENT DOCUMENTS

| | | | |
|---|---|---|---|
| JP | 9-512912 A | | 12/1997 |
| JP | 2006-343297 A | | 12/2006 |
| JP | 2007017407 A | * | 1/2007 |
| JP | 2008-32651 A | | 2/2008 |
| JP | 2008-145288 A | | 6/2008 |
| JP | 2009-80100 A | | 4/2009 |
| JP | 2009-115781 A | | 5/2009 |
| JP | 2012-002805 A | | 1/2012 |
| JP | 2012-189579 A | | 10/2012 |

OTHER PUBLICATIONS

Communication dated Dec. 21, 2015, issued by the Japan Patent Office in corresponding Japanese Application No. 2013-239722.

* cited by examiner

GAS SENSOR

BACKGROUND OF THE INVENTION

The present invention relates to a gas sensor having a sensor element exposed to a gas under measurement so as to detect a specific gas component in the gas under measurement and, more particularly, to a gas sensor having a sensor element formed with a porous protection layer.

Hereinafter, the term "front" refers to a gas sensing side with respect to the direction of an axis of a gas sensor; and the term "rear" refers to a side opposite the front side.

Conventionally known is a gas sensor of the type mounted for use on an exhaust pipe of an internal combustion engine etc. and equipped with a sensor element to generate an electromotive force or electrical resistance according to the concentration of a specific gas component such as NOx (nitrogen oxide) or oxygen in an exhaust gas of the internal combustion engine. The sensor element has a detection portion formed on a front end part thereof and adapted to, when heated to a predetermined high temperature by a heater etc., detect the specific gas component. Under such a high-temperature state, however, there is a fear of breakage (e.g. cracking) of the sensor element due to thermal impact at the time when water drops contained in the exhaust gas adhere to the detection portion of the sensor element (i.e. the detection portion of the sensor element gets wet with water). A gas sensor is thus developed in which a sensor element has a detection portion covered with a porous protection layer and protected from water as disclosed in Japanese Laid-Open Patent Publication No. 2009-115781.

More specifically, Japanese Laid-Open Patent Publication No. 2009-115781 discloses a gas sensor that includes a metal shell (metal housing) 1100, a ceramic holder 300 formed of an insulating ceramic material (such as alumina) and placed in an axial inner hole 1100h of the metal shell 1100 and a sensor element 21 held in an insertion hole 320 of the ceramic holder 300 as shown in FIG. 8. The sensor element 21 has, at a front end part thereof, a detection portion covered with a protection layer 25. The detecting portion with the protection layer 25 protrudes toward the front from the ceramic holder 31 such that a rear end part 26 of the protection layer 25 is accommodated within the axial inner hole 1100h of the metal shell 1100. Further, metallic protector members (protection tubes) 510 and 610 are attached to a front end portion of the metal shell 110 so as to protect therein the sensor element 21. In order to prevent the protection layer 25 from being damaged by collision with the ceramic holder 300 during insertion of the sensor element 21 into the insertion hole 320 of the ceramic holder 300, the rear end part 26 of the protection layer 25 is situated in front of and spaced apart from a front end of the insertion hole 320 of the ceramic holder 300. Thus, a side surface P of the sensor element 21 between the insertion hole 320 of the ceramic holder 300 and the rear end part 26 of the protection layer 25 is left uncovered and unprotected by the protection layer 25.

SUMMARY OF THE INVENTION

In the gas sensor of FIG. 8, a relatively large space remains between an inner circumferential surface 1100i of the metal shell 1100 and an outer surface of the sensor element 21 (protection layer 25); and a front-facing surface 300a of the ceramic holder 300 extends radially (as a horizontal plane) at a position corresponding to the side surface P of the sensor element 21. This allows, when water W enters into the inside of the protector member 510 through vent holes 560 and 670 of the protector members 510 and 610, the water W to run to the ceramic holder 300 along the inner circumferential surface 1100i of the metal shell 1100, easily move to the sensor element 21 from the front-facing surface 300a of the ceramic holder 300 and adhere to the side surface P of the sensor element 21. As the side surface P of the sensor element 21 is not covered with the protection layer 25, there is a fear of breakage (e.g. cracking) of the sensor element 21 due to thermal impact by the adhesion of the water W to such an uncovered side surface P of the sensor element 21.

In view of the above circumstance, it is conceivable to utilize a metal shell 1200 having an axial inner hole 1200h reduced in diameter as shown in FIG. 9. In this case, the space between an inner circumferential surface 1200i of the metal shell 1200 and the outer surface of the sensor element 21 (protection layer 25) decreases so that it becomes difficult for water W to enter into the axial inner hole 1200h of the metal shell 1200. In addition, a front-facing surface 1200k of the metal shell 1200 extends radially at a position corresponding to the rear end part of the protection layer 25 so that the water moves from the front-facing surface 1200k of the metal shell 1200 to the sensor element 21 and adhere to the protection layer 25. The water W can be thus prevented from adhering to the uncovered side surface P of the sensor element 21. However, the radiation of heat from the sensor element 21 to the metal shell 1200 via the axial inner hole 1200h is promoted by decrease of the space between the inner circumferential surface 1200i of the metal shell 1200 and the outer surface of the sensor element 21 (protection layer 25). This makes it difficult to maintain the sensor element 21 at a high temperature and thereby raises a problem of deterioration in the detection performance of the sensor element 21 or a need for more power supply to maintain the sensor element 21 at a high temperature.

The present invention has been made to solve the above-mentioned problems. It is an object of the present invention to provide a gas sensor in which a sensor element has a detection portion covered with a protection layer so as to prevent water from adhering to a part of the sensor element located at a rear side with respect to the protection layer without causing deterioration in detection performance and increase in power supply.

According to one aspect, of the present invention, there is provided a gas sensor comprising: a sensor element extending in an axis direction of the gas sensor, the sensor element having a detection portion formed at a front end part thereof to detect a specific gas component in a gas under measurement and a porous protection layer covering the detection portion; a cylindrical ceramic holder having an insertion hole through which a part of the sensor element located at a rear side with respect to the protection layer is inserted and surrounding a radial circumference of the sensor element; and a metal shell having an axial inner hole in which the ceramic holder is placed, the axial inner hole including a small-diameter hole located in a front end side thereof and a large-diameter hole located at a rear side with respect to the small-diameter hole and made larger in diameter than the small-diameter hole, the metal shell surrounding a radial circumference of the ceramic holder by engagement of a front-facing surface of the ceramic holder with a rear-facing surface of the metal shell defined between an inner surface of the small-diameter hole and an inner surface of the large-diameter hole, wherein the ceramic holder has a recessed hole formed with a larger diameter than the insertion hole and recessed toward the rear from the front-facing surface of the ceramic holder so as to be in communication with a front end of the insertion hole; wherein a rear end part of the protection layer is accommodated in the recessed hole with a space left between an inner circumferential surface of the recessed hole and an outer surface of the sensor element; and wherein the ceramic holder has a front circumferential edge defined between the inner circumferential surface of the recessed hole and the front-facing surface of the ceramic holder such that the whole of the front circumferential edge is located radially inside with respect to the inner surface of the small-diameter hole.

As mentioned above, the gas sensor according to one aspect of the present invention is so configured in that: the recessed hole is recessed toward the rear from the front-facing surface of the ceramic holder; the rear end part of the protection layer is accommodated in the recessed hole of the ceramic holder with some space left therebetween; and the whole of the front circumferential edge of the ceramic holder is located radially inside with respect to the inner surface of the small-diameter hole of the metal shell.

With such a configuration, the space between the inner circumferential surface (inner circumferential edge) of the recessed hole of the ceramic holder and the outer surface of the sensor element is made smaller than the space between the inner surface of the small-diameter hole of the metal shell and the outer surface of the sensor element. This makes it difficult that, even when water enters into the gas sensor and runs to the ceramic holder along the inner surface of the small-diameter hole of the metal shell, the water gets into the recessed hole of the ceramic holder. Further, the front-facing surface of the ceramic holder extends radially at the position corresponding to the protection layer so that the water moves to the sensor element from the front-facing surface of the ceramic holder and then adheres to the protection layer. The water can be thus prevented from adhering to a part of the sensor element located at the rear side with respect to the protection layer. It is therefore possible to relieve thermal shock on the sensor element and assuredly prevent breakage (e.g. cracking) of the sensor element.

Moreover, the space between the sensor element and the ceramic holder is decreased by the formation of the recessed hole in the ceramic holder. As is different from the metal shell, the ceramic holder can retard heat radiation thereto from the sensor element so as to maintain the sensor element at a high temperature. It is therefore possible to avoid deterioration in the detection performance of the sensor element and achieve reduction in the power consumption of the sensor element.

In one aspect of the present invention, it is preferable that the ceramic holder has a protruding portion protruding to the front of a circumferential edge of the metal shell defined between the rear-facing surface of the metal shell and the inner surface of the small-diameter hole. This allows, when the water runs to the ceramic holder along the inner surface of the small-diameter hole and moves to the sensor element from the front-facing surface of the ceramic holder, the protruding portion to force the water toward the front and thereby makes it more difficult that the water gets in the space between the inner circumferential surface of the recessed hole and the outer surface of the sensor element. Thus, the water can be more assuredly prevented from adhering to the part of the sensor element located at the rear side with respect to the protection layer.

It is also preferable in one aspect of the present invention that the inner circumferential surface of the recessed hole is in parallel to the axis direction or in a tapered form decreasing in diameter toward the rear. This facilitates removal of the ceramic holder from the molding die for improvement in the productivity of the ceramic holder.

It is accordingly possible in the present invention to not only prevent the adhesion of water to the part of the sensor element located at the rear side with respect to the protection layer but also avoid deterioration in the detection performance and achieve reduction in power consumption.

The other objects and features of the present invention will also become understood from the following description.

DESCRIPTION OF THE EMBODIMENTS

The present invention will be described below with reference to FIGS. 1 to 9. The following embodiment specifically refers to, as a gas sensor 1, a wide range oxygen sensor mounted on an exhaust pipe of an internal combustion engine and adapted to detecting the concentration of oxygen in an exhaust gas (as a gas under measurement) flowing through the exhaust pipe.

First, the overall structure of the gas sensor 1 will be explained below.

Figure 1:
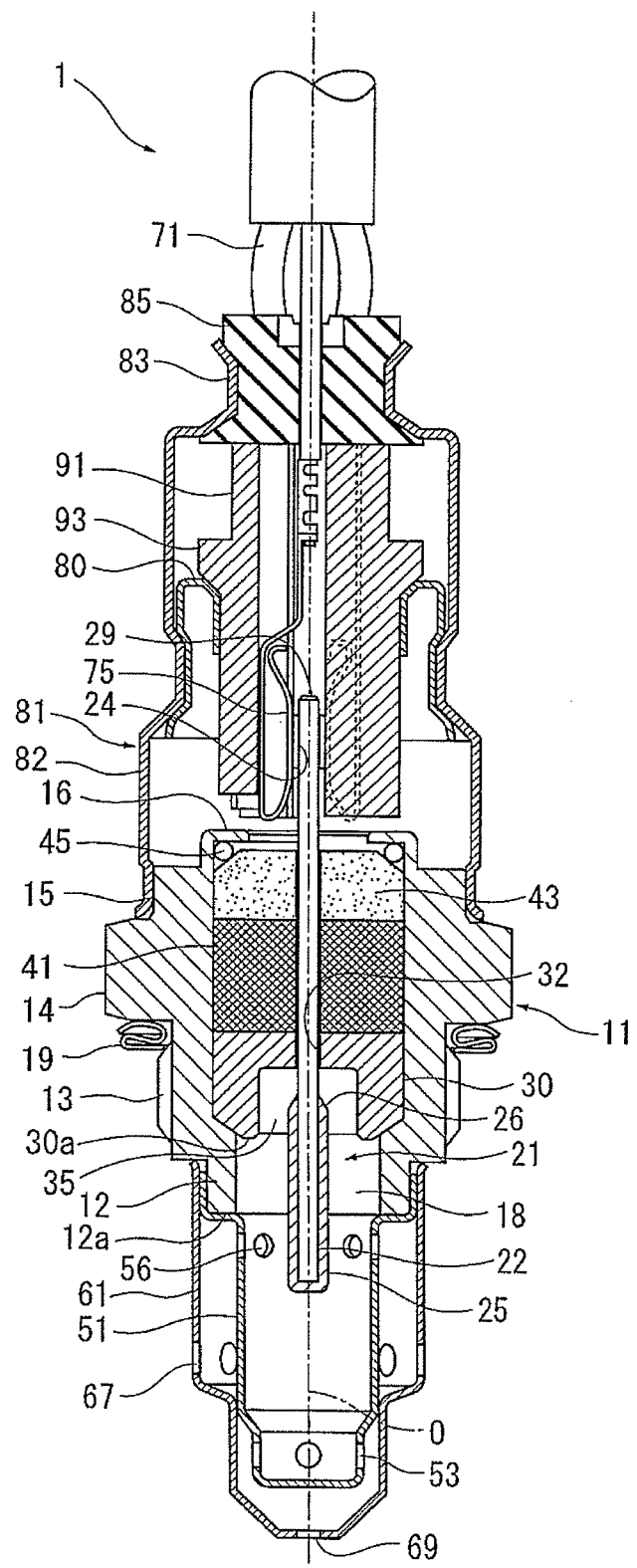
FIG. 1 is a section view of a gas sensor according to one embodiment of the present invention.

As shown in FIG. 1, the gas sensor 1 includes a sensor element 21 extending in the direction of an axis O of the gas sensor 1, a ceramic holder 30 having an insertion hole 32 through which the sensor element 21 is inserted and a metal shell (metal housing) 11 surrounding a radial circumference of the ceramic holder 30. A front end 23 and its vicinity (referred to as "front end part") of the sensor element 21 protrudes toward the front from a front-facing surface 30a of the ceramic holder 30 (see FIGS. 2 and 4). A detection portion 22 is formed on the front end part of the sensor element 21. A seal material 41 (such as formed body of talc), an insulating sleeve 43 and a ring washer 45 are placed in this order on a rear-facing surface of the ceramic holder 30 within the metal shell 11 so that, when the seal material 41 is axially compressed by pushing the insulating sleeve 43 and the ring washer 45, the sensor element 21 is hermetically fixed by the ceramic holder 30 in the metal shell 11 via the seal material 41, the insulating sleeve 43 and the ring washer 45. A rear end 29 and its vicinity (referred to as "rear end part") of the sensor element 21 protrudes toward the rear from the insulating sleeve 43 and from the metal shell 11. Electrode terminals 24 are formed on the rear end part of the sensor element 21 and respectively electrically connected to leads 71 by crimp contacts 75. The gas sensor 1 also includes a double-layer protector (explained later in detail) attached to the metal shell 11 so as to protect therein the front end part of the sensor element 21 and a protection tube 81 attached to the metal shell 11 so as to protect therein the rear end part of the sensor element 21 (including the electrode terminals 24). The leads 71 are drawn to the outside from a rear end of the protection tube 81 through a seal member 85.

Next, the respective structural components of the gas sensor 1 will be explained in more detail below.

The sensor element 21 is formed into an elongated, rectangular cross-section plate shape in the direction of the axis O. The detection portion 22 is provided on the front end part of the sensor element 21 and exposed to the gas under measurement to detect the specific gas component in the gas under measurement. In the present embodiment, the sensor element 21 is predominantly composed of ceramic (solid electrolyte) and is of known configuration. More specifically, the sensor element 21 has a solid electrolyte material (member) laminated on a ceramic material (substrate) and a pair of detection electrodes (not shown) formed on a front end side of the solid electrolyte material so as to constitute the detection portion 22. The sensor element 21 also has a porous protection layer 25 formed of a porous material such as alumina or spinel so as to cover the detection portion 22. Herein, the lateral cross section of the front end part of the sensor element 21 on which the protection layer 25 is formed is larger by a thickness of the protection layer 25 (e.g. 0.5 to 0.6 mm) than that of the part of the sensor element 21 located at the rear side with respect to the protection layer 25. (In the drawings, the thickness of the protection layer 25 is exaggerated for purposes of illustration.) Further, the lateral cross section of the part of the sensor element 21 located at the rear side with respect to the protection layer 25 is of uniform rectangular shape throughout its length (see FIG. 3). The sensor element 21 further includes a heater (not shown) embedded in the ceramic material so as to correspond in position to the detection portion 22. The electrode terminals 24 are formed on the rear end part of the sensor element 21 and connected to the respective leads 71 for signal output from the detection portion 22 and for power supply to the heater. Although not shown in the drawings, the electrode terminals 24 are generally elongated rectangular in shape. Two or three electrode terminals 24 are arranged side by side on each of opposite plate surfaces of the rear end part of the sensor element 21.

The metal shell 11 is formed into a different-diameter cylindrical shape in the direction of the axis O and includes a cylindrical (annular) front end portion 12 formed with a small diameter and around which the double-layer protector is fixed by welding. A thread 13 of larger outer diameter than the front end portion 12 is made on an outer circumferential surface of the metal shell 11 at a rear position with respect to the front end portion 12. The metal shell 11 also includes a polygonal portion 14 located at the rear side with respect to the thread 13 for mounting the gas sensor 1 onto the exhaust pipe by screwing the thread 13 into the mounting hole, a cylindrical portion 15 located at the rear side with respect to the polygonal portion 14 and around which the protection tube 81 is fixed by welding and a cylindrical rear end portion 16 located at the rear side with respect to the cylindrical portion 15 and made smaller in outer diameter than the cylindrical portion 15 and smaller in thickness for crimping. In FIG. 1, the rear end portion 16 of the metal shell 11 is radially inwardly bent by crimping. A gasket 19 is fitted on a front-facing surface of the polygonal portion 14 so as to, when the gas sensor 1 is mounted on the exhaust pipe, provide a seal the gas sensor 1 and the exhaust pipe.

Figure 2:
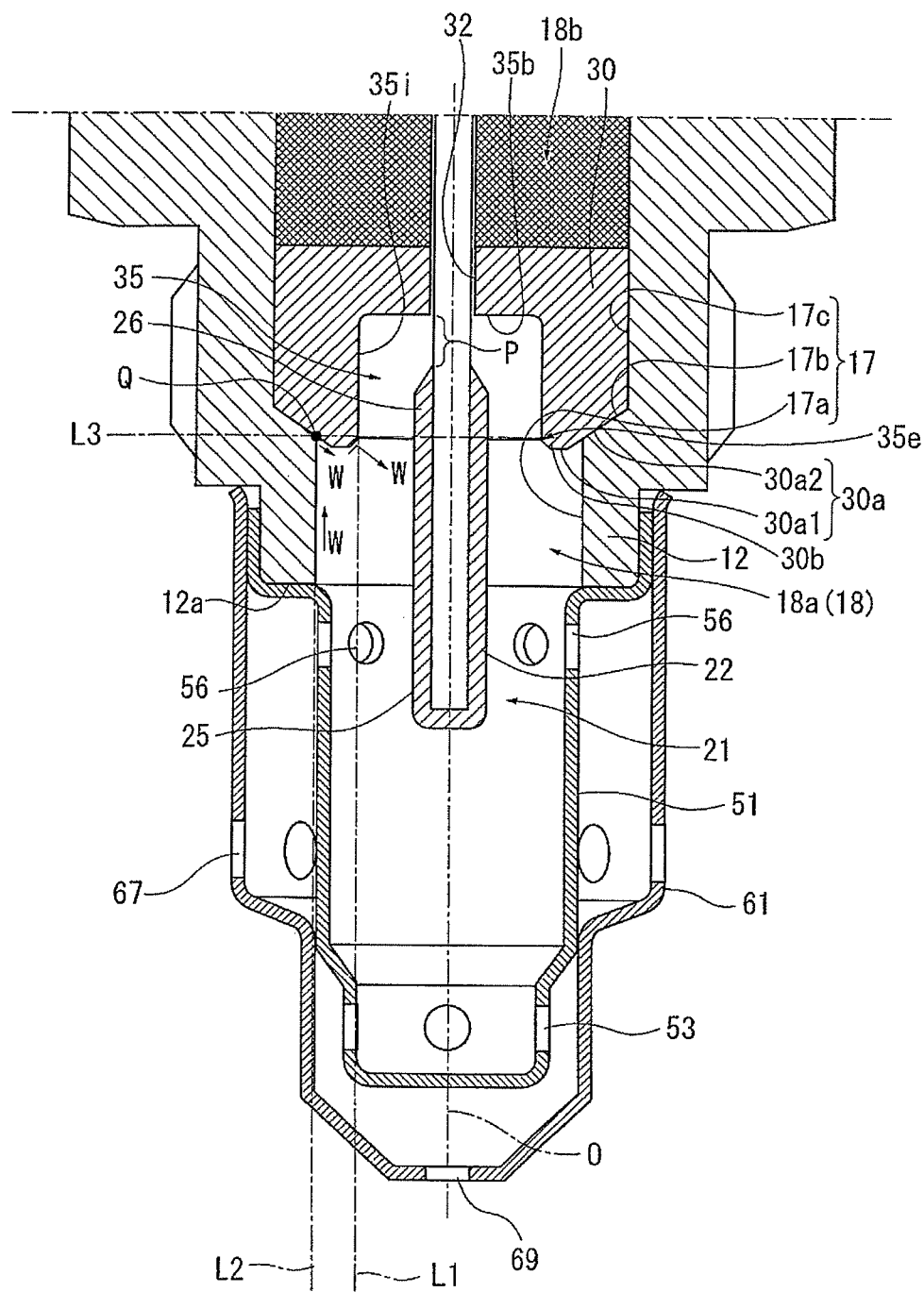
FIG. 2 is an enlarged section view of part of the gas sensor of FIG. 1.

An axial inner hole 18 is formed through the metal shell 11 in the direction of the axis O as shown in FIG. 2. The axial inner hole 18 includes a small-diameter hole 18a located in a front end side thereof and a large-diameter hole 18b located at the rear side with respect to the small-diameter hole 18a and made larger in diameter than the small-diameter hole 18a. There is thus defined a rear-facing surface 17b between an inner surface 17a of the small-diameter hole 18a and an inner surface 17c of the large-diameter hole 18b. In the present embodiment, the rear-facing surface 17b is in a tapered form decreasing in diameter toward the front. The inner surface 17a, the rear-facing surface 17b and the inner surface 17c constitute an inner circumferential surface 17 of the metal shell 11.

The ceramic holder 30 is formed of an insulating ceramic material such as alumina in a substantially cylindrical shape and placed in the large-diameter hole 18b of the metal shell 11. As shown in FIG. 2, the front-facing surface 30a of the ceramic holder 30 includes an outer front-facing surface region 30a2 in a tapered form decreasing in diameter toward the front and an inner front-facing surface region 30a1 made flat and located radially inside with respect to the outer front-facing surface region 30a2. The ceramic holder 30 is fixed in position and clearance-fitted in the metal shell 11 by engagement of a radially outer side of the outer front-facing surface region 30a2 with the rear-facing surface 17b of the metal shell 11.

The insertion hole 32 is formed through the center of the ceramic holder 30 in the direction of the axis O and has a rectangular opening of substantially the same dimensions as those of the lateral cross section of the part of the sensor element 21 located at the rear side with respect to the protection layer 25 such that the part of the sensor element 21 located at the rear side with respect to the protection layer 25 can be inserted through the insertion hole 32 with almost no clearance left therebetween.

As shown in FIG. 2, the ceramic holder 30 also has a recessed hole 35 recessed toward the rear side from the inner front-facing surface region 30a1 so as to be in communication with a front end of the insertion hole 32. In the present embodiment, the recessed hole 35 is formed into a circular shape with a larger diameter than the insertion hole 32. A bottom surface 35b of the recessed hole 35 (corresponding in position to the front end of the insertion hole 32) is made flat, whereas an inner circumferential surface 35i of the recessed hole 35 is in parallel to the direction of the axis O. There is a front circumferential edge 35e defined at a position between the inner circumferential surface 35i of the recessed hole 35 and the inner front-facing surface region 30a1 of the ceramic holder 30. In the present embodiment, a part of the inner front-facing surface region 30a1 located adjacent to the front circumferential edge 35 is chamfered.

The double-layer protector is provided with inner and outer protector members (protection tubes) 51 and 61 as shown in FIGS. 1 and 2. Each of the inner and outer protector members 51 and 61 has a bottomed cylindrical shape. A rear end portion of the inner protector member 51 is fitted around and welded to the front end portion 12 of the metal shell 11. A plurality of circumferentially spaced vent holes 56 (e.g. eight vent holes) are formed in a rear end side of the inner protector member 51, whereas a plurality of circumferentially spaced discharge holes 53 (e.g. four discharge holes) are formed in a front end side of the inner protector member 51. A rear end portion of the outer protector member 61 is fitted around the rear end portion of the inner protector member 51 and welded to the front end portion 12 of the metal shell 11. A plurality of circumferentially spaced vent holes 67 (e.g. eight vent holes) are formed in a front end side of the outer protector member 61, whereas a discharge hole 69 is formed in the center of a front end of the outer protector member 61.

In the present embodiment, the sensor element 21 is inserted through the insertion hole 32 of the ceramic holder 30, with the front end of the sensor element 21 protruding toward the front from the front-facing surface 30a of the ceramic holder 30 and from a front end 12a of the metal shell 11 and with a rear end part 26 of the protection layer 25 being accommodated in the recessed hole 35, as shown in FIGS. 1 and 2. In order to prevent the protection layer 25 from being damaged by collision with the ceramic holder 30 during insertion of the sensor element 21 into the insertion hole 32 of the ceramic holder 30, the rear end part 26 of the protection layer 25 is preferably situated in front of and spaced apart from the front end of the insertion hole 32 (i.e. the bottom surface 35b of the recessed hole 35). Besides, the rear end part 26 of the protection layer 25 accommodated in the recessed hole 35 is made axially shorter in length than the other portion of the protection layer 25 located outside of the recessed hole 35 in order to avoid deterioration in the detection performance of the sensor element 21.

Figure 3:
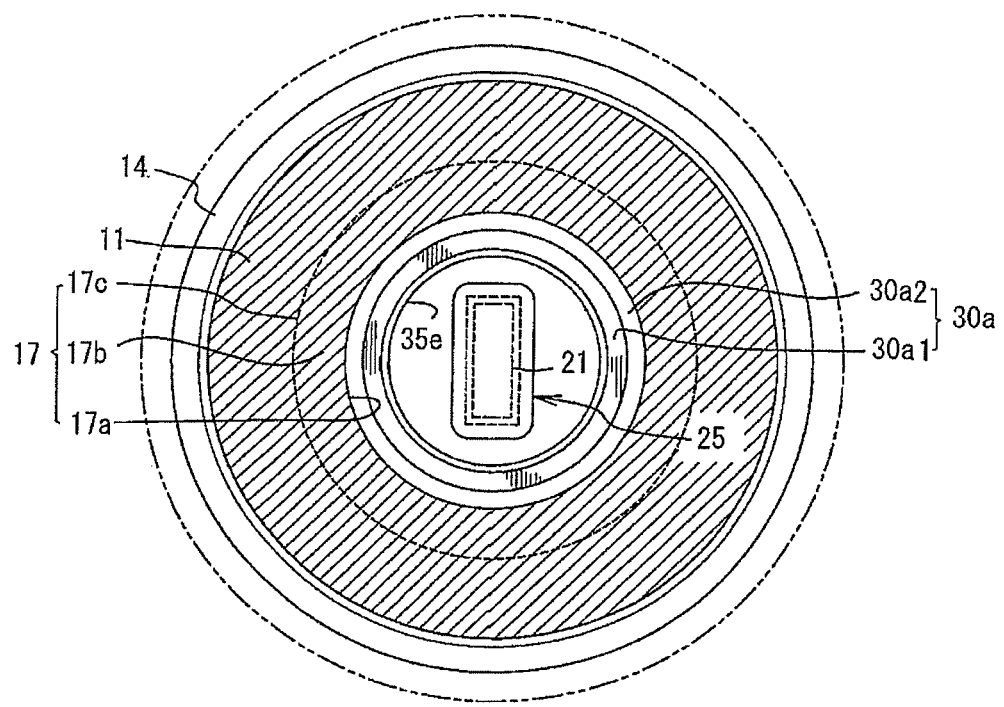
FIG. 3 is a schematic view of a ceramic holder (recessed portion), when viewed from the front through a metal shell, of the gas sensor of FIG. 1.

Furthermore, the entire inner circumferential surface 35i of the recessed hole 35 is situated apart from an outer circumferential surface of the rear end part 26 of the protection layer 25 accommodated in the recessed hole 35 and, at the same time, located radially inside with respect to an inner circumferential surface 51a of the inner protector member 51 (that is, located radially inside with respect to the innermost circumferential part of the double-layer protector directly facing the sensor element 21) in the present embodiment. In other words, the whole of the front circumferential edge 35e of the recessed hole 35 is visually recognized as shown in FIG. 3 when viewed from the front in the direction of the axis O through the small-diameter hole 18 of the metal shell 11 by detachment of the protector members 51 and 61. In the present embodiment, the inner circumferential surface 35i of the recessed hole 35 is parallel to the direction of the axis O so that the distance from the axis O to a radial position L1 of the front circumferential edge 35e of the recessed hole 35 is uniform at not only the front circumferential edge 35e of the recessed hole 35 but also any point on the inner circumferential surface 35i of the recessed hole 35 as shown in FIG. 2. The inner surface 17a of the small-diameter hole 18a is also in parallel to the direction of the axis O so that the distance from the axis O to a radial position L2 of the inner surface 17a of the small-diameter hole 18a of the metal shell 11 is uniform at any point on the inner surface 17a of the small-diameter hole 18a as shown in FIG. 2 in the present embodiment. It is herein noted that, in the case where the inner surface 17a of the small-diameter hole 18a is not in parallel to the direction of the axis O, the radial position L2 refers to the radially innermost position at which the diameter of the inner surface 17a of the small-diameter hole 18a is the smallest in the direction of the axis O. When the whole of the whole of the front circumferential edge 35e of the recessed hole 35 is visually recognized, the distance from the axis O to the position L2 is larger than the distance from the axis O to the position L1 (i.e. L2>L1) at any circumferential point. If the distance from the axis O to the position L2 is smaller than or equal to than the distance from the axis O to the position L1 (i.e. L2≤L1), a part of the front circumferential edge 35e of the recessed hole 35 is not visually recognized.

As shown in FIG. 1, the crimp contacts 75 are attached to the front ends of the leads 71 and crimped onto the electrode terminals 24 of the sensor element 21 under their respective spring action so as to make electrical connection between the electrode terminals 24 and the leads 71. In the present embodiment, a crimp contact holding member 91 of ceramic material is placed in the protection tube 81. Crimp contact accommodation holes are formed in the crimp contact holding member 91 such that the crimp contacts 75 are held in an opposed arrangement through the respective crimp contact accommodation holes. Further, an annular supporting member 80 is fixed in the protection tube 81 so as to restrict radial or frontward movement of the crimp contact holding member 91.

The protection tube 81 is formed of a metal material in a different-diameter cylindrical shape. A large-diameter cylindrical front end portion 82 of the protection tube 81 is fitted around and welded to the cylindrical portion 15 of the metal shell 11 so that the rear end part of the gas sensor 1 is hermetically covered by the protection tube 81

The seal member 85 is formed of e.g. a rubber material and fitted in a small-diameter cylindrical rear end portion 83 of the protection tube 81. Lead insertion holes are formed in the seal member 85 such that the leads 71 are drawn to the outside through the respective lead insertion holes. The seal member 85 is compressed by radially inwardly crimping the small-diameter cylindrical rear end portion 83 of the protection tube 81 so as to hermetically close the rear end opening of the outer tube 81.

As mentioned above, the gas sensor 1 is so configured that: the recessed hole 35 is recessed toward the rear from the front-facing surface 30a of the ceramic holder 30; the rear end part 26 of the protection layer 25 is accommodated in the recessed hole 35 of the ceramic holder 30 with a space left therebetween; and the whole of the front circumferential edge 35e of the ceramic holder 30 is located radially inside with respect to the inner surface 17a of the small-diameter hole 18a of the metal shell 11.

With such a configuration, the space between the inner circumferential surface 35e of the recessed hole 35 of the ceramic holder 30 and the outer surface of the sensor element 21 is made smaller than the space between the inner surface 17a of the small-diameter hole 18 of the metal shell 11 and the outer surface of the sensor element 21. This makes it difficult that, even when water W enters into the inside of the gas sensor 1 through the vent holes 56 and 67 of the protector members 51 and 61 and runs to the ceramic holder 30 along the inner surface 17a of the small-diameter hole 18a of the metal shell 11, the water W gets into the recessed hole 35 of the ceramic holder 30. Further, the front-facing surface 30a extends radially at the position corresponding to the protection layer 25 of the sensor element 21 so that the water W moves to the sensor element 21 from the front-facing surface 30a of the ceramic holder 30 and then adheres to the protection layer 25. The water W can be thus prevented from adhering to a side surface P of the sensor element 21 uncovered by the protection layer 25. It is therefore possible to assuredly prevent breakage (e.g. cracking) of the sensor element 21 due to thermal impact by the adhesion of the water W.

Moreover, the space between the sensor element 21 and the ceramic holder 30 can be made smaller by the formation of the recessed hole 35 in the ceramic holder 30. As is different from the metal shell 11, the ceramic holder 31 can retard heat radiation thereto from the sensor element 21 so as to maintain the sensor element 21 at a high temperature. It is therefore possible to avoid deterioration in the detection performance of the sensor element 21 and achieve reduction in the power consumption of the sensor element 21.

As shown in FIG. 2, there is a circumferential edge Q between the rear-facing surface 17b of the metal shell 11 and the inner surface 17a of the small-diameter hole 18a at an axial position L3. In the present embodiment, the ceramic holder 30 has a protruding portion 30b protruding to the front of the axial position L3. This allows, when the water W runs to the ceramic holder 30 along the inner surface 18a of the small-diameter hole 17a and moves to the sensor element 21 from the front-facing surface 30a of the ceramic holder 31, the protruding portion 31b to force the water W toward the front and thereby makes it more difficult that the water W gets in the space between the inner circumferential surface 35i of the recessed hole 35 and the outer surface of the sensor element 21. Thus, the water W can be more assuredly prevented from adhering to the side surface P of the sensor element 21.

In the gas sensor 1, the seal material 41 is pressed toward the front by the insulating sleeve and axially compressed when the rear end portion 16 of the metal shell 11 is crimped radially inwardly via the ring washer 45. The sensor element 21 is thus hermetically fixed by the ceramic holder 30 in the metal shell 11 via the seal material 41, the insulating sleeve 43 and the ring washer 45 as mentioned above.

The assembling of the above-structured gas sensor 1 (including the mounting of the sensor element 21) will be explained below.

Figure 4:
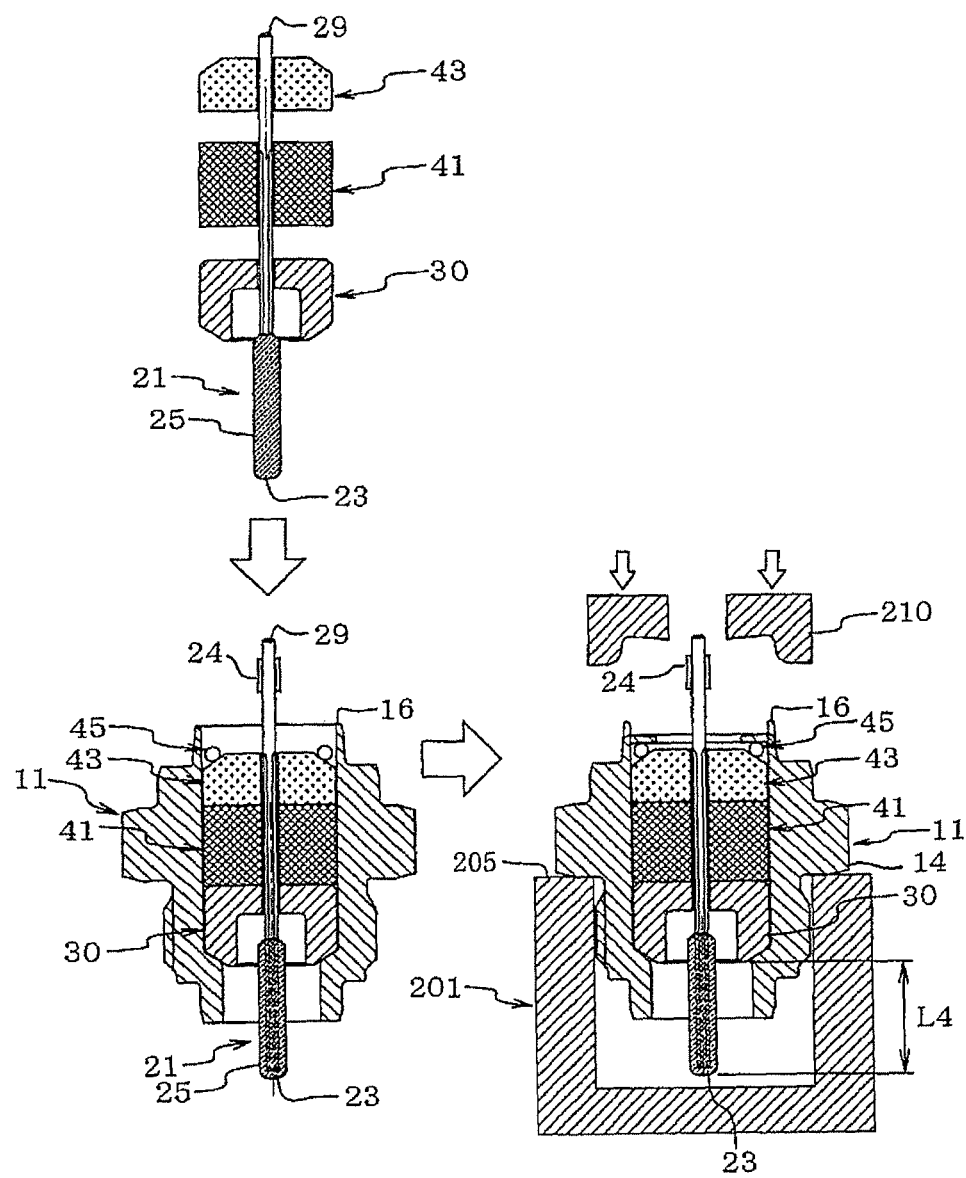
FIG. 4 is a schematic view showing a step of fixing a sensor element to the metal shell during manufacturing of the gas sensor of FIG. 1.

As shown in the upper-left side of FIG. 4, the rear end part of the sensor element 21 is inserted through the ceramic holder 30, the seal material 41 and the insulating sleeve 43. The resulting subassembly unit is inserted and placed in the axial inner hole 18 of the metal shell 11 as shown in the lower-left side of FIG. 4. The ring washer 45 is arranged on a rear end of the insulating sleeve 43 within the inside of the rear end portion 16 of the metal shell 11. At this stage, the front end 23 of the sensor element 21 protrudes by an appropriate amount (length).

Then, the metal shell 11 is placed and held in position win a jig 201 as shown in the right side of FIG. 4 by contact of a front-facing surface of the polygonal portion 14 of the metal shell 11 with a positioning portion 205 of the jig 201. When the rear end portion 16 of the metal shell 11 is bent and crimped radially inwardly toward the front by a crimping die 210, the seal material 41 and the insulating sleeve 43 are axially compressed to push the ceramic holder 30 in which the sensor element 21 is inserted. Thus, the sensor element 21, the ceramic holder 30 etc. are fixed in the metal shell 11 with the front end 23 of the sensor element 21 protruding by a length L4 from the front end of the ceramic holder 30. It is noted that, although not specifically shown in the drawings, each of the seal material 41 and the insulating sleeve 43 has an elongated rectangular hole corresponding in shape to the lateral cross section of the sensor element 21 (as viewed in the direction of the axis O), before the compression, as in the case of the ceramic holder 30.

Figure 5:
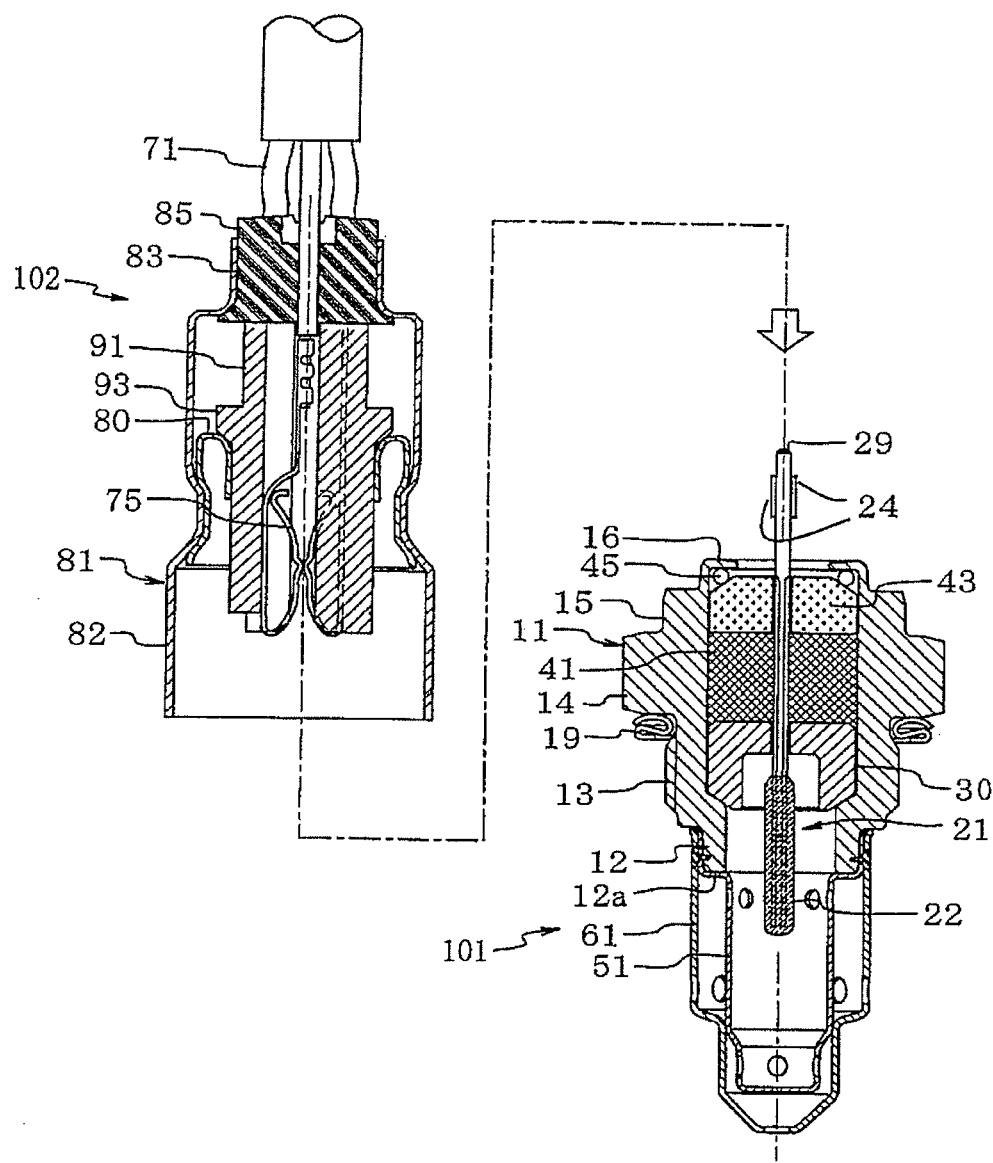
FIG. 5 is a schematic view showing a final assembling step during manufacturing of the gas sensor of FIG. 1.

As shown in FIG. 5, the above-obtained subassembly unit is processed into a front-side subassembly unit 101 by welding the protector members 51 and 61 to the metal shell 11 and fitting the gasket 19 on the metal shell 11; whereas rear-side subassembly unit 102 is obtained by assembling the other respective sensor structural components together. These subassembly units 101 and 102 are combined together by arranging the subassembly units 101 and 102 coaxially with each other and fitting the subassembly unit 201 into the subassembly unit 102. When the protruding rear end part of the sensor element 21, on which the electrode terminals 24 have been formed, is inserted between the opposed crimp contacts 75 in the crimp contact holding member 91, the crimp contacts 75 are crimped to the electrode terminals 24 under their respective spring action. The large-diameter cylindrical front end portion 82 of the protection tube 81 is fitted around the cylindrical portion 15 of the metal shell 11. The entire circumference of the overlap part between the front end portion 82 of the protection tube 81 and the cylindrical portion 15 of the metal shell 11 is then subjected to laser welding. By this, the gas sensor 1 of FIG. 1 is completed.

The entire contents of Japanese Patent Application No. 2013-239722 (filed on Nov. 20, 2013) and No. 2013-106474 (filed on May 20, 2013) are herein incorporated by reference.

Although the present invention has been described with reference to the above specific embodiment, the present invention is not limited to such a specific embodiment. Various modifications and variations can be made to the above embodiment without departing from the scope of the present invention.

For example, the shape of the ceramic holder 30, the shapes of the recessed hole 35 and the front-facing surface 30a of the ceramic holder 30 and the shape of the inner hole 17 of the metal shell 11 are not limited those described above.

Figure 6:
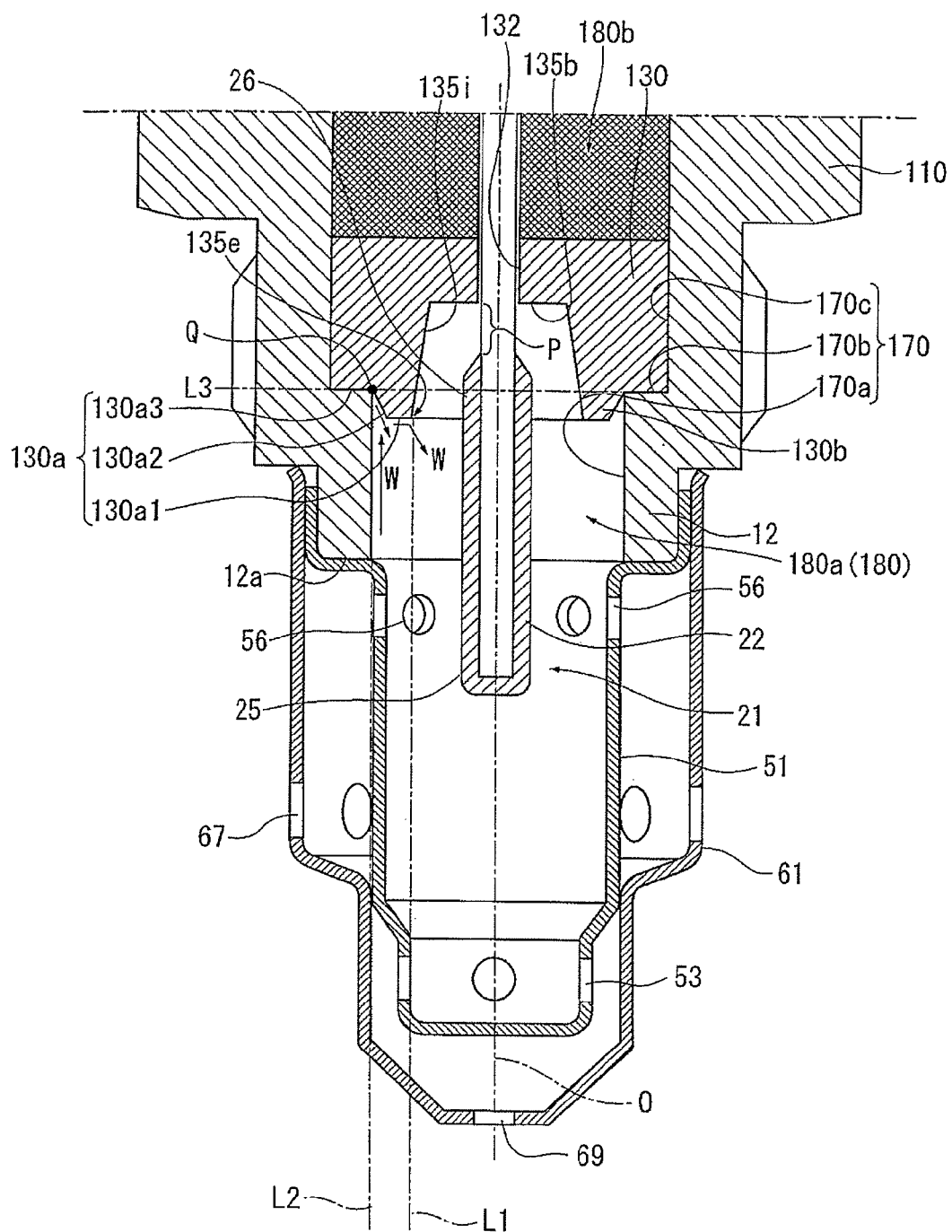
FIG. 6 is an enlarged section view of a modification of the gas sensor of FIG. 1.

As shown in FIG. 6, it is feasible to provide a metal shell 110 and a ceramic holder 130 as a modification example of the above embodiment.

In the modification example of FIG. 6, an axial inner hole 180 of the metal shell 110 includes a small-diameter hole 180a and a large diameter hole 180b such that, among an inner circumferential surface 170 of the metal shell 110, a rear-facing surface 170b is defined as a flat horizontal surface between an inner surface 170a of the small-diameter hole 180a and an inner surface 170c of the large-diameter hole 180b. On the other hand, a front-facing surface 130a of the ceramic holder 130 includes a flat outer front-facing surface region 130a3 for engagement with the flat rear-facing surface 170 of the metal shell 110, and intermediate front-facing surface region 130a2 located radially inside of the outer front-facing surface region 130a3 and provided in a tapered form decreasing in diameter toward the front and a flat inner front-facing surface region 130a1 located radially inside of the intermediate front-facing surface region 130a2. The ceramic holder 130 is thus fixed in position and clearance-fitted in the axial inner hole 180 of the metal shell 11 by engagement of the flat outer front-facing surface region 130a3 of the ceramic holder 130 with the flat rear-facing surface 170b of the metal shell 110.

As in the case of the above embodiment, the ceramic holder 130 has a recessed hole 135 recessed toward the rear from the front-facing surface 130a in the modification example of FIG. 6. There is a front circumferential edge 135e defined between an inner circumferential surface 135i of the recessed hole 135 and the inner front-facing surface region 130a1 of the ceramic holder 130 such that the whole of the front circumferential edge 135e of the recessed hole 135 is located radially inside of the inner surface 170a of the small-diameter hole 180a of the metal shell 110. In other words, the whole of the front circumferential edge 135e of the recessed hole 135 is visually recognized when viewed from the front in the direction of the axis O through the metal shell 110 by detachment of the protector members 51 and 61.

Further, the ceramic holder 130 has a protruding portion 130b protruding toward the front from the axial position L3 of a circumferential edge Q between the rear-facing surface 170b of the metal shell 110 and the inner surface 170a of the small-diameter hole 180a in the modification example of FIG. 6 as in the case of the above embodiment.

In the modification example of FIG. 6, the inner circumferential surface 135i of the recessed hole 135 is in a tapered form decreasing in diameter toward the rear although the inner circumferential surface 35i of the recessed hole 35 is in parallel to the direction of the axis O in the above embodiment. In general, the ceramic holder 30, 130 is produced by die molding a ceramic material and firing the resulting molded body. If the inner circumferential surface 35$i$, 135$i$ of the recessed hole 35, 135 is tapered down (decreased in diameter) toward the front, it becomes difficult to remove the ceramic holder 30, 130 (molded body) from the molding die. This leads to a need to use a split die etc. and thereby causes increase in cost. It is thus preferable that the inner circumferential surface 35$i$, 135$i$ of the recessed hole 35, 135 is in parallel to the direction of the axis O or in a tapered form decreasing in diameter toward the rear.

In the above embodiment, both of the outer circumferential surface of the ceramic holder 30 and the inner circumferential surface 35$i$ of the recessed hole 35 are circular in shape when viewed from the front, in order to ensure uniform wall thickness and prevent distortion of the ceramic holder 30 caused due to variations in thickness during the formation of the ceramic holder 30 by sintering.

In general, the insertion hole of the ceramic insulator is formed corresponding in shape and size to the lateral cross section of the sensor element such that the sensor element can be inserted through the insertion hole of the ceramic holder with almost no clearance (or slight clearance) left therebetween. In the case where the sensor element has an elongated plate shape (or square bar shape) of rectangular cross section, the insertion hole of the ceramic holder is formed into a rectangular shape corresponding to the rectangular cross section of the sensor element. In the case where the sensor element has a rod shape of circular cross section, the insertion hole of the ceramic holder is formed into a circular shape corresponding to the circular cross section of the sensor element. By contrast, the ceramic insulator itself is formed of a ceramic material in e.g. a cylindrical shape with a circular outer circumference in view of electrical insulation and heat resistance. For these reasons, it is preferable that the ceramic insulator has an outer circumferential surface of circular shape and, at the same time, the recessed hole of the ceramic insulator has an inner circumferential surface of cylindrical shape when viewed from the front in order to secure uniformity in wall thickness and prevent sintering distortion and stress concentration.

Figure 7:
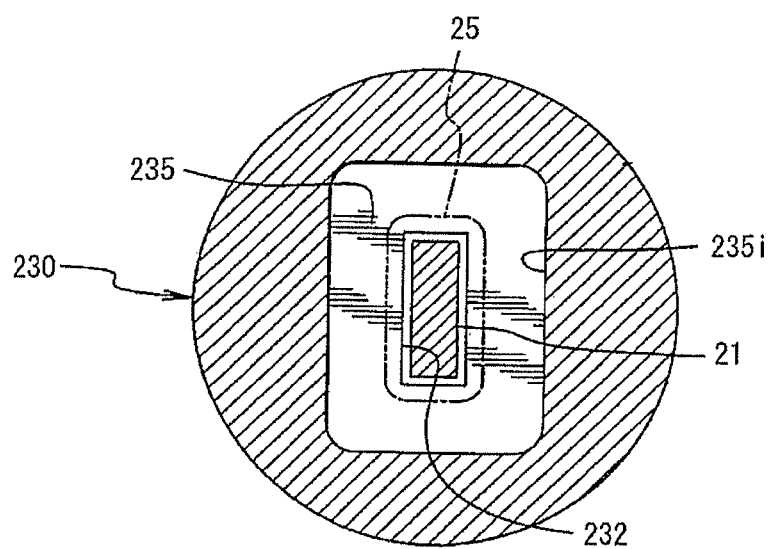
FIG. 7 is a bottom view of a modification of the ceramic holder in the gas sensor of FIG. 1.
Figure 8:
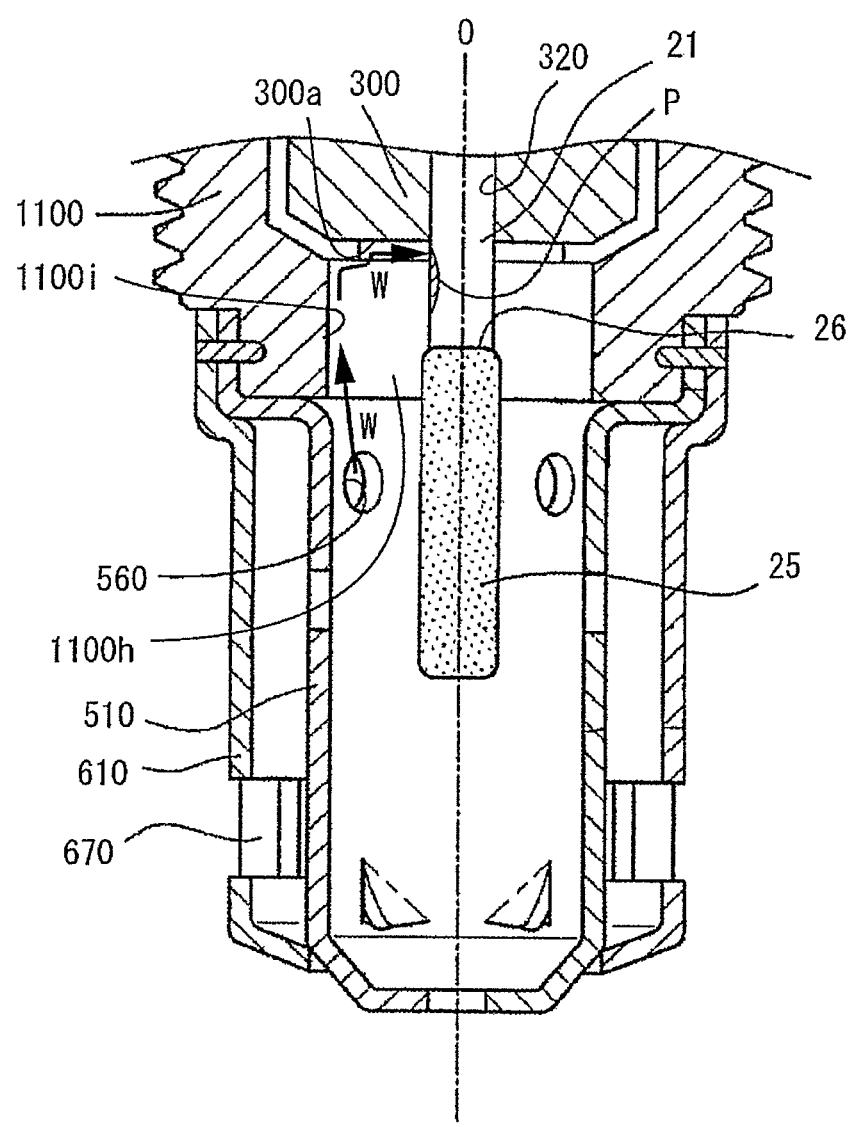
FIG. 8 is an enlarged section view of part of a conventional gas sensor.
Figure 9:
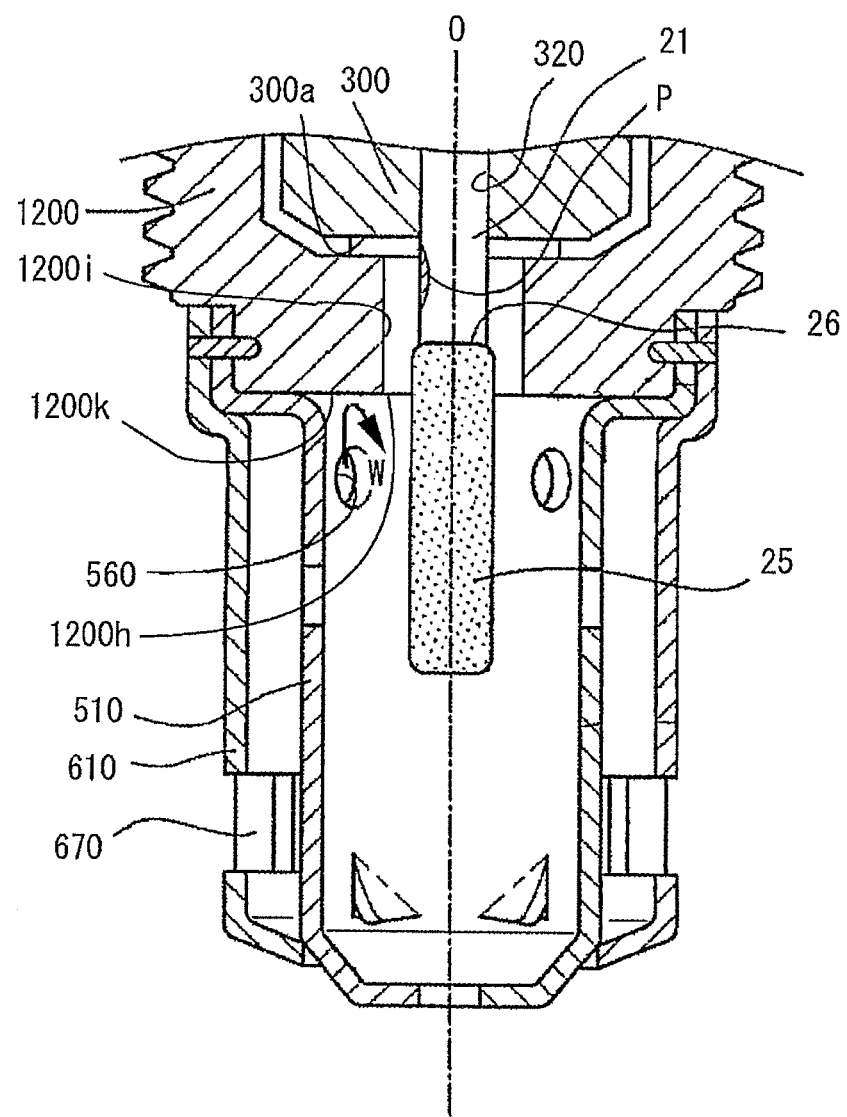
FIG. 9 is an enlarged section view of part of another conventional gas sensor.

For example, it is feasible to provide a ceramic holder 230 with a recessed hole 235 such that an inner circumferential surface 235$i$ of the recessed hole 235 is polygonal (e.g. rectangular) in shape as viewed from the front as shown in FIG. 7. In this case, the inner circumferential surface 235$i$ of the recessed hole 235 is preferably formed into a polygonal shape having as many sides as possible and thereby being as close as possible to a circle so that the wall thickness of the recessed hole 235 can be made as uniform as possible for improvement of the strength of the ceramic holder 230 and prevention of sintering distortion of the ceramic holder 230.

Although the sensor element 21 is rectangular in cross section in the above embodiment, the sensor element 21 may alternatively be shaped into any other cross section such as square cross section.

In the above embodiment, the present invention is embodied as the wide range oxygen sensor. The present invention is not however limited to such an oxygen sensor and can be applied to various types of gas sensors.

The scope of the invention is defined with reference to the following claims.

What is claimed is:

1. A gas sensor, comprising:
   a sensor element extending in an axis direction of the gas sensor, the sensor element having a detection portion formed at a front end part thereof to detect a specific gas component in a gas under measurement and a porous protection layer covering the detection portion;
   a cylindrical ceramic holder having an insertion hole through which a part of the sensor element located at a rear side with respect to the protection layer is inserted and surrounding a radial circumference of the sensor element; and
   a metal shell having an axial inner hole in which the ceramic holder is placed, the axial inner hole including a small-diameter hole located in a front end side thereof and a large-diameter hole located at a rear side with respect to the small-diameter hole and made larger in diameter than the small-diameter hole, the metal shell surrounding a radial circumference of the ceramic holder by engagement of a front-facing surface of the ceramic holder with a rear-facing surface of the metal shell defined between an inner surface of the small-diameter hole and an inner surface of the large-diameter hole,
   wherein the ceramic holder has a recessed hole formed with a larger diameter than the insertion hole and recessed toward the rear from the front-facing surface of the ceramic holder so as to be in communication with a front end of the insertion hole;
   wherein a rear end part of the protection layer is accommodated in the recessed hole with a space left between an inner circumferential surface of the recessed hole and an outer surface of the sensor element; and
   wherein the ceramic holder has a front circumferential edge defined between the inner circumferential surface of the recessed hole and the front-facing surface of the ceramic holder such that the whole of the front circumferential edge is located radially inside with respect to the inner surface of the small-diameter hole.

2. The gas sensor according to claim 1, wherein the ceramic holder has a protruding portion protruding to the front of a circumferential edge of the metal shell defined between the rear-facing surface of the metal shell and the inner surface of the small-diameter hole.

3. The gas sensor according to claim 1, wherein the inner circumferential surface of the recessed hole is in parallel to the axis direction or in a tapered form decreasing in diameter toward the rear.

4. The gas sensor according to claim 2, wherein the inner circumferential surface of the recessed hole is in parallel to the axis direction or in a tapered form decreasing in diameter toward the rear.

* * * * *